US009827107B1

(12) United States Patent
Arnin

(10) Patent No.: US 9,827,107 B1
(45) Date of Patent: Nov. 28, 2017

(54) ADJUSTABLE SPINAL CAGE

(71) Applicant: Apifix Ltd., Carmiel (IL)

(72) Inventor: Uri Arnin, Kiryat Tivon (IL)

(73) Assignee: Apifix Ltd., Carmiel (IL)

( * ) Notice: Subject to any disclaimer, the term of this patent is extended or adjusted under 35 U.S.C. 154(b) by 0 days.

(21) Appl. No.: 15/158,737

(22) Filed: May 19, 2016

(51) Int. Cl.
*A61F 2/44* (2006.01)
*A61F 2/46* (2006.01)

(52) U.S. Cl.
CPC .......... *A61F 2/4425* (2013.01); *A61F 2/4611* (2013.01)

(58) Field of Classification Search
CPC ............................ A61F 2/4425; A61F 2/4611
USPC ........ 623/17.11, 17.15, 17.16; 606/246, 279, 606/99, 86 A
See application file for complete search history.

(56) References Cited

U.S. PATENT DOCUMENTS 4,759,769 A 7/1988 Hedman
6,641,614 B1 * 11/2003 Wagner ................ A61F 2/4455 623/17.15
6,685,742 B1 * 2/2004 Jackson ................. A61F 2/447 623/17.11
7,655,012 B2 * 2/2010 DiPoto ................ A61B 1/3135 600/201
2005/0125061 A1 * 6/2005 Zucherman .......... A61F 2/4425 623/17.11
2013/0158663 A1 * 6/2013 Miller .................. A61F 2/4425 623/17.16
2013/0158664 A1 * 6/2013 Palmatier ............... A61F 2/447 623/17.16
2014/0330387 A1 * 11/2014 Arnin ................ A61B 17/7001 623/17.16
2014/0343678 A1 * 11/2014 Suddaby ................. A61F 2/46 623/17.16
2016/0022434 A1 * 1/2016 Robinson ............... A61F 2/447 623/17.16
2016/0030190 A1 2/2016 Robinson

FOREIGN PATENT DOCUMENTS

WO 98/14142 4/1998
WO 98/48739 11/1998
WO 2014/152337 9/2014
WO 2014/186384 11/2014

OTHER PUBLICATIONS

PCT Search Report and Written Opinion PCT/IB2016/051800, received Jan. 13, 2017.

* cited by examiner

*Primary Examiner* — Pedro Philogene
*Assistant Examiner* — David C Comstock
(74) *Attorney, Agent, or Firm* — Dekel Patent Ltd.; David Klein

(57) ABSTRACT

A spinal cage includes a first support plate pivotally connected to a second support plate by a hinge, and a plate mover actuated by an actuator and located between the first and second support plates. The plate mover is arranged to slide against an inclined surface on the first support plate. A hinge is journaled in an elongate aperture formed in a hinge housing protruding from first support plate, the hinge being free to translate and rotate in the elongate aperture.

10 Claims, 3 Drawing Sheets

12 26 24 20 16 18 22 14

26 12 20 24 18 16 22 14

ADJUSTABLE SPINAL CAGE

FIELD OF THE INVENTION

The present invention relates generally to spinal implants and prostheses, and particularly to an expandable and rotatable spinal cage, for example, with a slidable hinge.

BACKGROUND OF THE INVENTION

Spine degeneration of different types is affecting significant portion of the population. Current surgical treatment involves many times the use of an intervertebral cage that is placed between two adjacent vertebrae.

As the anatomy is different from case to case, and as inserting a small implant is always easier than placing a bigger one, a cage that can be inserted between the vertebrae in a small configuration and adjusted in situ to fit the anatomy is a clear need.

SUMMARY OF THE INVENTION

The present invention seeks to provide an improved expandable spinal cage, which, for example, can control the lordosis angle between two vertebrae after being installed in a contracted configuration.

In one embodiment of the present invention, the expandable cage has a slidably supported hinge, as is described more in detail hereinbelow.

There is thus provided in accordance with a non-limiting embodiment of the present invention a spinal cage including a first support plate pivotally connected to a second support plate by a hinge, a plate mover actuated by an actuator and located between the first and second support plates, the plate mover being arranged to slide against an inclined surface on the first support plate, and a hinge journaled in an elongate aperture formed in a hinge housing protruding from first support plate, the hinge being free to translate and rotate in the elongate aperture.

In accordance with an embodiment of the present invention one or more support members are biased towards the hinge and/or the first support plate. The one or more support members may be biased by a biasing device.

In accordance with an embodiment of the present invention the inclined surface has different slopes at different portions thereof.

In accordance with an embodiment of the present invention the plate mover has different slopes at different portions thereof.

In accordance with an embodiment of the present invention one or more keels extend from the first support plate and/or the second support plate.

In accordance with an embodiment of the present invention inner ramps are provided on which the first support plate moves.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
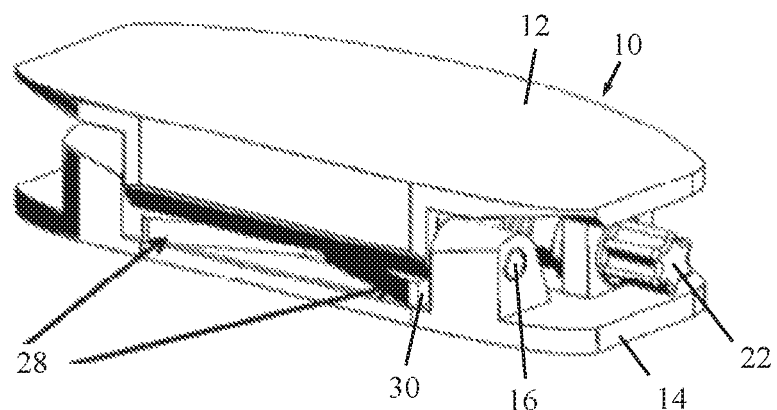
FIG. 1 is a simplified pictorial illustration of a spinal cage, in an initial, contracted configuration, constructed and operative in accordance with a non-limiting embodiment of the invention.
Figure 2:
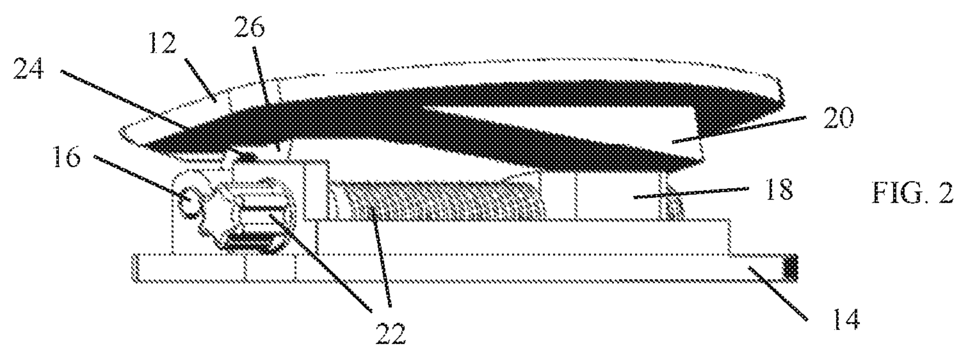
FIGS. 2 and 3 are simplified pictorial and end-view illustrations, respectively, of the cage of FIG. 1 in an expanded configuration, in which the cage has been lifted and tilted to a new height and tilt angle (e.g., for achieving a desired height and lordosis angle)
Figure 3:
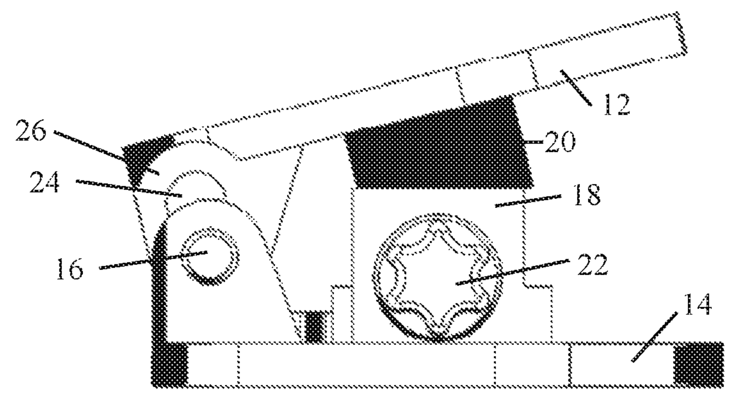
Figure 4:
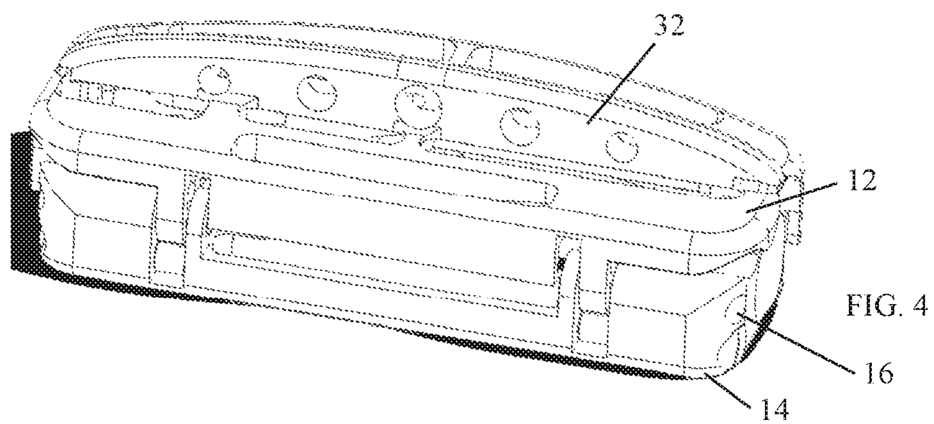
FIG. 4 is a simplified pictorial illustration of a spinal cage, in an initial, contracted configuration, constructed and operative in accordance with another non-limiting embodiment of the invention.

Reference is now made to FIGS. 1-3, which illustrate a spinal cage 10, constructed and operative in accordance with a non-limiting embodiment of the invention.

Spinal cage 10 includes a first support plate 12 and a second support plate 14, which may be (but not necessarily) initially parallel to each other. First support plate 12 is pivotally connected to second support plate 14 by a hinge 16. A plate mover 18 is located between first and second support plates 12 and 14. Plate mover 18 may be a wedge with an inclined surface or other suitable pushing structure that may be flat or curved (any geometrical shape). Plate mover 18 is arranged to slide against an inclined surface 20 (having any geometrical shape) on (e.g., the underside of) first support plate 12. As will be described below, the action of plate mover 18 sliding against inclined surface 20 causes first support plate 12 to be lifted and/or tilted with respect to second support plate 14.

Inclined surface 20 (as well as plate mover 18) can have different slopes (in terms of depth, angle, length, shape, size, etc.) at different portions along its length or width.

Plate mover 18 may be actuated by an actuator 22, such as a linear actuator (e.g., a control screw threaded through a boss protruding from second support plate 14). Actuator 22 may be manually operated (e.g., by turning an appropriate screwdriver that mates with the head of the control screw) or automatically operated (e.g., actuator 22 may be a motor, locally or remotely operated, which turns the control screw, such as with feedback from sensors in a control loop).

Hinge 16 is journaled in an elongate aperture 24 (e.g., oval or elliptical aperture) formed in a hinge housing 26 protruding from first support plate 12. Hinge 16 is free to translate and rotate in elongate aperture 24.

In accordance with a non-limiting embodiment of the invention, one or more support members 28 may be biased towards hinge 16 and/or first support plate 12. The support members 28 may be made of a flexible material or may be urged by a biasing device 30 (e.g., a leaf spring or coil spring) Initially, when the spinal cage 10 is in its contracted configuration, the support members 28 simply abut against hinge 16 and/or first support plate 12. After first support plate 12 is lifted and/or tilted with respect to second support plate 14, a gap is formed between hinge 16 and second support plate 14, and/or between first support plate 12 and second support plate 14, and the support members 28 are urged by the biasing force into this gap. In this manner, the support members 28 support and maintain first support plate 12 in its expanded configuration (lifted and/or tilted). The one or more support members 28 may move in translation and/or rotation (e.g., about a pivot).

Figure 5:
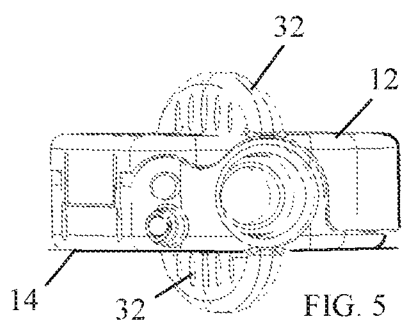
FIGS. 5, 6 and 7 are simplified end-view illustrations of the cage of FIG. 4 in respective contracted, expanded height and expanded height plus tilt configurations.
Figure 6:
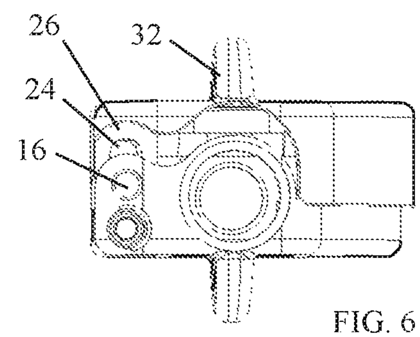
Figure 7:
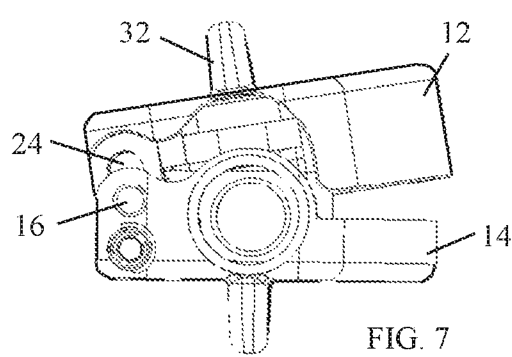

Reference is now made to FIGS. 4-7, which illustrate spinal cage 10 with one or more keels 32 extending (e.g., at right angles) from first support plate 12 and/or second support plate 14. The keels 32 may be used to ensure proper installation orientation of the cage in the spinal structure. FIGS. 5-7 illustrate cage 10 respectively in contracted, expanded height and expanded height plus tilt configurations.

Figure 8:
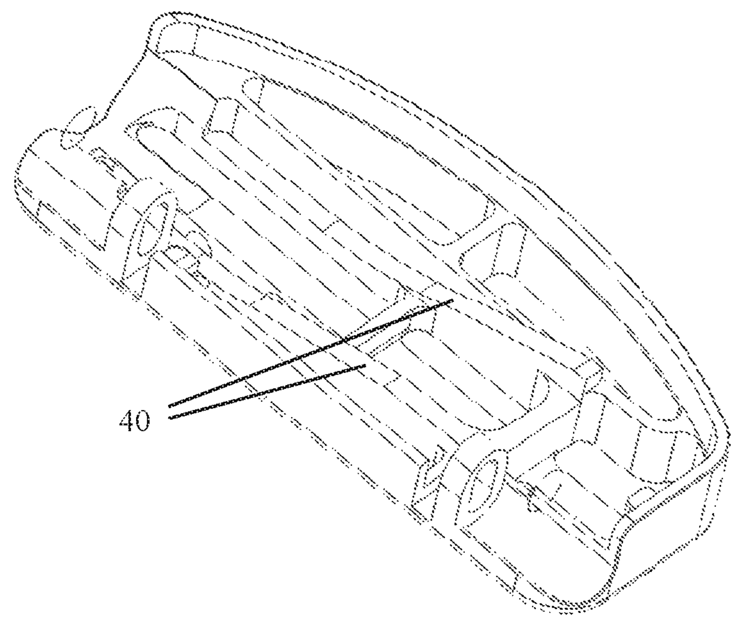
FIGS. 8 and 9 are simplified pictorial and side-view illustrations, respectively, inner ramps in the cage, which determine the way in which the plates tilt and move with respect to each other.
Figure 9:
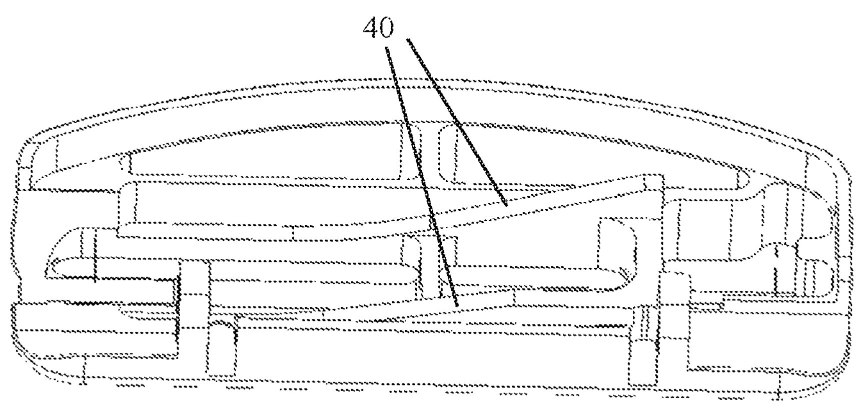

Reference is now made to FIGS. 8 and 9, which illustrate one or more inner ramps 40 in the cage 10 on which first support plate 12 moves, which determine the way in which the plates 12 and 14 tilt and move with respect to each other. Ramps 40 serve as the inclined surface 20 or may be in addition to another inclined surface. As seen in the illustrated embodiment, the inclined portion of one of the ramps may have a different length, height, shape or angle than another of the ramps. The hinge and first support plate may slide upwards on one of the ramps until the hinge reaches its highest position in the elongate aperture. Afterwards, sliding continues on the other ramp or ramps to cause tilting of the first support plate. The ramps thus help achieve the desired lordosis angle.

Figure 10:
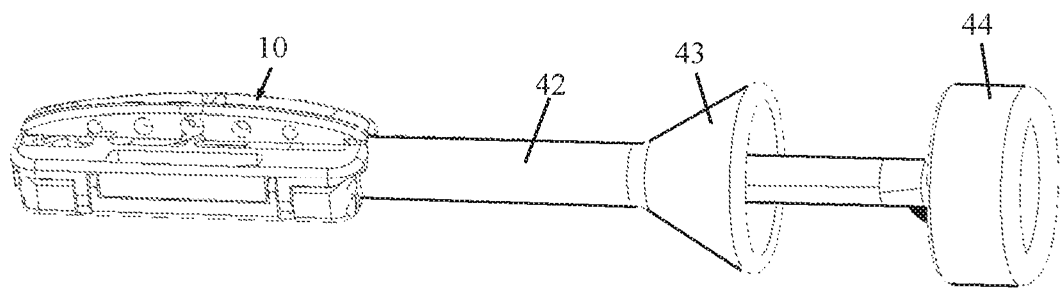
FIG. 10 is a simplified pictorial illustration of an applicator tool and an adjustment tool for installing the spinal cage, constructed and operative in accordance with a non-limiting embodiment of the invention.

Reference is now made to FIG. 10 is a simplified pictorial illustration of an applicator tool 42 and an adjustment tool 44 for installing the spinal cage, constructed and operative in accordance with a non-limiting embodiment of the invention.

The applicator tool 42 may be a tube with a proximal funnel 43. The adjustment tool 44 may be a screwdriver for turning the actuator, for example. Cage 10 may be attached to the distal portion of applicator tool 42 (such as by a male-female connection, threaded connection, or any other suitable connection) Applicator tool 42 grasps the cage 10 during insertion in the disc space or other structure. The adjustment tool 44 may be inserted through the tube of the applicator tool 42 to reach the actuator. After cage 10 is expanded in situ, the adjustment tool 44 is removed. After lifting or tilting the first support plate, bone graft, collagen or other materials may be added into the spinal cage, such as below the first support plate.

What is claimed is:

1. A spinal cage comprising:

a first support plate pivotally connected to a second support plate by a hinge;

a plate mover actuated by an actuator and located between said first and second support plates, said plate mover being arranged to slide against an inclined surface on said first support plate;

a hinge journaled in an elongate aperture formed in a hinge housing protruding from first support plate, said hinge being free to translate and rotate in said elongate aperture; and one or more support members biased towards said hinge and/or said first support plate, wherein when said first support plate is lifted and/or tilted with respect to said second support plate, a gap is formed between said hinge and said second support plate, and/or between said first support plate and said second support plate, and said one or more support members are urged by a biasing force to move into said gap.

2. The spinal cage according to claim 1, wherein said one or more support members are made of a flexible material.

3. The spinal cage according to claim 1, wherein said one or more support members are biased by a biasing device comprising a spring.

4. The spinal cage according to claim 1, wherein said inclined surface has different slopes at different portions thereof.

5. The spinal cage according to claim 1, wherein said plate mover has different slopes at different portions thereof.

6. The spinal cage according to claim 1, further comprising one or more keels extending from said first support plate and/or said second support plate.

7. The spinal cage according to claim 1, further comprising inner ramps on which said first support plate moves.

8. The spinal cage according to claim 1, further comprising an applicator tool with a proximal funnel and an adjustment tool for passing through said applicator tool.

9. The spinal cage according to claim 1, wherein when the spinal cage is in a contracted configuration, said one or more support members abut against said hinge and/or said first support plate.

10. The spinal cage according to claim 1, wherein said one or more support members move in translation and/or rotation.

* * * * *